US011806317B2

(12) United States Patent
Lin et al.

(10) Patent No.: US 11,806,317 B2
(45) Date of Patent: Nov. 7, 2023

(54) COMPOSITION CAPABLE OF PROMOTING TESTOSTERONE SECRETION AND USE THEREOF

(71) Applicant: TCI CO., LTD, Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/499,350

(22) PCT Filed: Apr. 3, 2018

(86) PCT No.: PCT/CN2018/081709
§ 371 (c)(1),
(2) Date: Sep. 30, 2019

(87) PCT Pub. No.: WO2018/184523
PCT Pub. Date: Oct. 11, 2018

(65) Prior Publication Data
US 2020/0030396 A1 Jan. 30, 2020

Related U.S. Application Data

(60) Provisional application No. 62/503,185, filed on May 8, 2017, provisional application No. 62/480,860, filed on Apr. 3, 2017.

(51) Int. Cl.
| | | |
|---|---|---|
| A61K 36/185 | (2006.01) | |
| A23L 33/105 | (2016.01) | |
| A61K 9/00 | (2006.01) | |
| A61K 9/08 | (2006.01) | |
| A61K 9/48 | (2006.01) | |
| A61P 3/04 | (2006.01) | |
| A61K 31/01 | (2006.01) | |
| A61K 31/015 | (2006.01) | |
| A61K 36/21 | (2006.01) | |
| A61K 36/258 | (2006.01) | |
| A61K 36/31 | (2006.01) | |
| A61K 36/45 | (2006.01) | |
| A61K 36/48 | (2006.01) | |
| A61K 36/53 | (2006.01) | |
| A61K 36/67 | (2006.01) | |
| A61K 36/73 | (2006.01) | |
| A61K 36/74 | (2006.01) | |
| A61K 36/752 | (2006.01) | |
| A61K 36/815 | (2006.01) | |
| A61K 36/82 | (2006.01) | |
| A61K 36/87 | (2006.01) | |
| A61K 36/886 | (2006.01) | |
| A61K 36/8962 | (2006.01) | |
| A61K 36/9066 | (2006.01) | |
| A61K 8/9789 | (2017.01) | |
| A61P 17/16 | (2006.01) | |
| A61Q 19/00 | (2006.01) | |
| A23F 3/16 | (2006.01) | |

(Continued)

(52) U.S. Cl.
CPC ............ *A61K 36/185* (2013.01); *A23F 3/163* (2013.01); *A23L 33/105* (2016.08); *A61K 8/97* (2013.01); *A61K 8/9789* (2017.08); *A61K 9/0056* (2013.01); *A61K 9/0095* (2013.01); *A61K 9/08* (2013.01); *A61K 9/48* (2013.01); *A61K 31/01* (2013.01); *A61K 31/015* (2013.01); *A61K 36/21* (2013.01); *A61K 36/258* (2013.01); *A61K 36/31* (2013.01); *A61K 36/45* (2013.01); *A61K 36/48* (2013.01); *A61K 36/53* (2013.01); *A61K 36/67* (2013.01); *A61K 36/73* (2013.01); *A61K 36/74* (2013.01); *A61K 36/752* (2013.01); *A61K 36/815* (2013.01); *A61K 36/82* (2013.01); *A61K 36/87* (2013.01); *A61K 36/886* (2013.01); *A61K 36/8962* (2013.01); *A61K 36/9066* (2013.01); *A61P 3/04* (2018.01); *A61P 17/16* (2018.01); *A61P 19/04* (2018.01); *A61Q 17/04* (2013.01); *A61Q 19/007* (2013.01); *A61Q 19/08* (2013.01); *A23V 2002/00* (2013.01)

(58) Field of Classification Search
CPC ...................................... A61K 36/00
USPC ........................................ 424/725
See application file for complete search history.

(56) References Cited

U.S. PATENT DOCUMENTS

2008/0260924 A1 10/2008 Chen et al.
2008/0268095 A1 10/2008 Herzog
(Continued)

FOREIGN PATENT DOCUMENTS

CN 1631268 * 6/2005
CN 101120792 A 2/2008
(Continued)

OTHER PUBLICATIONS

Harvard Health Publishing, Testosterone—What it does and doesn't do, 2105.*
Qiu-Feng et al. Acta Veterinaria et Zootechnica Sinica, 2014, 45 (3), 410-416.*
High testosterone levels in women, 2021.*
Examination report dated Jan. 12, 2023, listed in correspondent China patent application No. 202210508157.X (publication No. CN114712476A).
(Continued)

*Primary Examiner* — Michael V Meller
(74) *Attorney, Agent, or Firm* — Chieh-Mei Wang

(57) ABSTRACT

A composition comprising a grape seed extract and a black tea extract. The composition can increase testosterone secretion more effectively than a single component, and can be used for preparing pharmaceutical compositions, foods, health foods, dietary supplements or drinks used for promoting testosterone secretion.

3 Claims, 2 Drawing Sheets

(51) Int. Cl.
   *A61K 8/97*   (2017.01)
   *A61Q 17/04*  (2006.01)
   *A61P 19/04*  (2006.01)
   *A61Q 19/08*  (2006.01)

(56) References Cited

U.S. PATENT DOCUMENTS

| | | | | |
|---|---|---|---|---|
| 2009/0092687 A1* | 4/2009 | Stein | ............... | A61K 31/56 424/728 |
| 2013/0295068 A1* | 11/2013 | Annerl | ............ | A61K 31/385 424/94.1 |
| 2013/0344215 A1* | 12/2013 | Young | ............... | A61P 3/04 426/542 |

FOREIGN PATENT DOCUMENTS

| | | | |
|---|---|---|---|
| CN | 101254206 | A | 9/2008 |
| CN | 101306000 | A | 11/2008 |
| CN | 101505615 | A | 8/2009 |
| CN | 101816360 | A | 9/2010 |
| CN | 101868243 | A | 10/2010 |
| CN | 102250741 | A | 11/2011 |
| CN | 102552562 | A | 7/2012 |
| CN | 102669344 | A | 9/2012 |
| CN | 103037883 | A | 4/2013 |
| CN | 103519267 | A | 1/2014 |
| CN | 103999901 | A | 8/2014 |
| CN | 104127594 | A | 11/2014 |
| CN | 104274439 | A | 1/2015 |
| CN | 104623670 | A | 5/2015 |
| CN | 104920692 | * | 9/2015 |
| CN | 105412354 | A | 3/2016 |
| CN | 105616243 | A | 6/2016 |
| CN | 105963208 | A | 9/2016 |
| CN | 105995696 | * | 10/2016 |
| CN | 106085749 | * | 11/2016 |
| CN | 106136066 | A | 11/2016 |
| CN | 106418546 | A | 2/2017 |
| DE | 202009002126 | U1 | 4/2009 |
| JP | 2002012542 | A | 1/2002 |
| JP | 2005176691 | A | 7/2005 |
| JP | 2008280310 | A | 11/2008 |
| TW | 200500013 | * | 1/2005 |

OTHER PUBLICATIONS

Examination report dated Feb. 15, 2023, listed in correspondent China patent application No. 202210511639.0 (publication No. CN114712412 A).
Examination report dated Feb. 21, 2023, listed in correspondent China patent application No. 202210511769.4 (publication No. CN114832024A).
Enhanced protective effects of combined treatment with B-carotene and curcumin against Hyperthermic Spermatogenic Disorders in mice, Lin et al., BioMed Research International, Dec. 31, 2016 pp. 1-8.
Effect of Lycopene upon sheep on testicle and androgen, Qu et al., Proceeding of the 7th China Academic Symposium of Food Nutrition, China Academic Journal Electronic Publishing House, Oct. 31, 2014 p. 462, abstract.
Essential substance: Five Natural Ways to Enhance the Level of Testosterone, Liu, Jan. 20, 2015 https://www.jianshu.com/p/3e5f162bf94e.
Dong, Zhengming et al., "Effects of Grape Seed Extract on Sex Hormones and VEGF in Human Prostate Cancer Cell Lines LNCaP and PC-3", Sep. 2010, vol. 25, No. 9, Journal of Clinical Urology.
Examination report dated Mar. 15, 2019, listed in correspondent Taiwan patent application No. 107111696 (publication no. TW 201836627).
Examination report dated Jan. 11, 2021, listed in correspondent China patent application No. 201880021757.5 (publication No. CN 110494150).
All about Testosterone, https://selfhacked.com/blog/testosterone-will-add/, Jul. 7, 2016.
Oxidative stress, Nutritional Antioxidants, and Testosterone Secretion in Men, Glade MJ et al., Annals of Nutritional Disorders & Therapy, 2015;2(1):1019.
Examination report dated Apr. 18, 2023, listed in correspondent China patent application No. 202210511849.X (publication No. CN 114832037 A).
Examination report dated Apr. 24, 2023, listed in correspondent China patent application No. 202210511634.8 (publication No. CN 114652780 A).
8 Scientific Ways to Boost Your Testosterone Levels Naturally, Feb. 7, 201, https://oxygn.cn/shenghuo/jiankang/2017/02/07/855.html, pp. 1-15, especially paragraph 1-3 of p. 13.
The Research about Status on Blueberry Industry and the Design of Blueberry-Plantation in GuangDong Province, Hualan Xiao, Feb. 15, 2016, Zhongkai University of Agriculture and Engineering, Guangzhou, China, pp. 8-9.
2014 Vity reward: Nature's plus Ultra T Male—the male sexual health formula, Jan. 30, 2015 http://www.123haitao.com/t/49123.
Examination report dated Jul. 19, 2023, listed in correspondent China patent application No. 202210511639.0 (publication No. CN 114712412 A).
Examination report dated Jul. 30, 2023, listed in correspondent China patent application No. 202210511635.2 (publication No. CN 114712430 A).
Examination report dated Aug. 26, 2023, listed in correspondent China patent application No. 202210511675.7 (publication No. CN 114652781 A).
Examination report dated Aug. 11, 2023, listed in correspondent China patent application No. 202210511419.8 (publication No. CN 114652776 A).
Effect of Different Addition Levels of β-carotene on Semen Quality and Serum Parameters in Holstein Bulls, Liu, Ru-Xiang et al., Jiangsu Agricultural Journal vol. 24, No. 6, 2008 pp. 862-866.
The effects of lycium barbarum juice to serum testosterone and sexual function in adult men, Xu, Guo-Qin et al., Pharmacy and Translational Journal, E-J Transl Med vol. 3, No. 4, 2016 pp. 66-69.
Complete Family Diet Health Handbook, Liao, Zhuo-Hua, People's Health Publishing House, Chinese Edition Library CIP Data HeZi, No. 053935, 2004.
The Government of India, the Biological Diversity, 2002.†

* cited by examiner
† cited by third party

COMPOSITION CAPABLE OF PROMOTING TESTOSTERONE SECRETION AND USE THEREOF

CROSS-REFERENCE TO RELATED APPLICATION

This application claims priority of U.S. patent application Ser. No. 62/480,860, filed on Apr. 3, 2017, and U.S. patent application Ser. No. 62/503,185, filed on May 8, 2017, the content of which is incorporated herein in its entirety by reference.

BACKGROUND OF THE INVENTION

1. Field of the Invention

The present invention relates to a composition comprising a plant extract and uses thereof, in particular to a composition for promoting secretion of testosterone and uses thereof.

2. The Prior Art

Testosterone is a steroid-derived hormone that is secreted primarily by male testes or female ovaries, and a small number of testosterone is secreted by the adrenal glands. Testosterone belongs to the main androgen and anabolic steroid in the body. It has important effects on health for both men and women, such as enhancing sexual desire, improving muscle mass and strength, enhancing immune function or maintaining bone density, and anti-osteoporosis.

In humans or vertebrates, testosterone can be converted to estradiol, which activates certain estrogen receptors and affects the growth of cartilage or the secretion of luteinizing hormone. In addition, testosterone can also activate androgen receptors directly or in the form of serum dihydrotestosterone (DHT), thereby promoting the performance of male hormone-related genes, increasing muscle mass and strength, and bone density and intensity, and can stimulate linear growth and bone maturity. On the other hand, in the male effect, testosterone can promote the sexual organ maturity and male secondary sexual characteristics.

Therefore, if the amount of testosterone secretion can be appropriately increased, it has a good effect on the appearance of male characteristics and the maintenance of sexual desire, further enhances the quality of muscles and the density of bones, and has a slowing effect on aging. However, the ingredients or drugs currently available to promote the increase in the amount of testosterone secretion are limited. If a certain plant extract is used, it must be administered at a relatively high dose, which has limitations in terms of cost of use and effect. Therefore, if a small amount of components of various extracts can be administered, a high dose effect of a single component can be produced, the use of the aforementioned effects can be greatly improved, and the cost of use can be reduced.

Among the plants or health-care ingredients that people often eat or drink, such as: extracts of grape seed, black tea, green tea, red wine, citrus, spinach, green coffee beans, blueberries, Pu-erh tea, Four seasons spring tea, broccoli sprouts, ginseng, wolfberry, aloe, turmeric, garlic, red clover, and rosemary, and apple polyphenols, beta carotene or lycopene, etc.. It is unknown whether the above components alone or in combination have the effect of promoting testosterone secretion. If a combination of components that can significantly increase the secretion of testosterone can be found from the complex composition, it will be good news for the relevant users.

SUMMARY OF THE INVENTION

A primary objective of the present invention is to provide a composition comprising a plant extract. By itself or as a pharmaceutical composition or a food composition, which can combine the effects of extracts and/or other components of various plants to significantly promote the concentration of testosterone secretion, thereby improving the performance of individuals in sexual characteristics, as well as the growth of muscle and bone quality.

According to an embodiment of the present invention, the composition comprises at least one combination selected from the group consisting of a grape seed extract and a black tea extract, a grape seed extract and a green tea extract, a grape seed extract and a citrus extract, a grape seed extract and a spinach extract, a red wine extract and a black tea extract, a red wine extract and a Pu-erh tea extract, a red wine extract and a Four Seasons Spring tea extract, a red wine extract and a spinach extract, a red wine extract and a green coffee bean extract, a red wine extract and a blueberry extract, a red wine extract and a grape seed extract, a citrus extract and a spinach extract, a citrus extract and a green coffee bean extract, a citrus extract and a red wine extract, a citrus extract and a blueberry extract, a citrus extract and a grape seed extract, a green coffee bean extract and a blueberry extract, a green coffee bean extract and a green tea extract, a green coffee bean extract and a spinach extract, a green coffee bean extract and a Pu-erh tea extract, a spinach extract and a green tea extract, a spinach extract and a citrus extract, a spinach extract and a Pu-erh tea extract, a spinach extract and a Four Seasons Spring tea extract, a spinach extract and a blueberry extract, a spinach extract and a grape seed extract, a broccoli sprout extract and lycopene, apple polyphenols and a turmeric extract, apple polyphenols and a broccoli sprout extract, beta carotene and a turmeric extract, beta carotene and lycopene, beta carotene and a broccoli sprout extract, a ginseng extract and a turmeric extract, a ginseng extract and lycopene, a ginseng extract and a broccoli sprout extract, a ginseng extract and beta carotene, a wolfberry extract and beta carotene, a wolfberry extract and a ginseng extract, an aloe extract and a red clover extract, a rosemary extract and a turmeric extract, a rosemary extract and a wolfberry extract, a rosemary extract and a garlic extract, and a rosemary extract and a red clover extract. That is, the composition of the embodiment of the present invention may be a combination of any one of the above groups, or a combination of two or more combinations.

According to an embodiment of the present invention, the combination comprises a component ratio ranging from 0.8-1.2:1.2-0.8, preferably 1:1.

Another objective of the present invention is to provide a pharmaceutical composition comprising the aforementioned composition and a pharmaceutically acceptable carrier.

According to an embodiment of the present invention, the pharmaceutical composition is in a form of a solution, a capsule or a lozenge.

Another objective of the present invention is to provide a food composition.

According to an embodiment of the present invention, the food composition comprises the aforementioned composition and a food ingredient, wherein the food ingredient is a component of a general food, a health food, a dietary supplement or a drink.

Another objective of the present invention is to provide a method for promoting secretion of testosterone, comprising administering to a subject in need thereof an effective amount of the aforementioned composition.

According to an embodiment of the present invention, the composition is a pharmaceutical composition for promoting secretion of testosterone.

According to an embodiment of the present invention, the composition is a food product, a health food, a dietary supplement or a drink for promoting secretion of testosterone.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
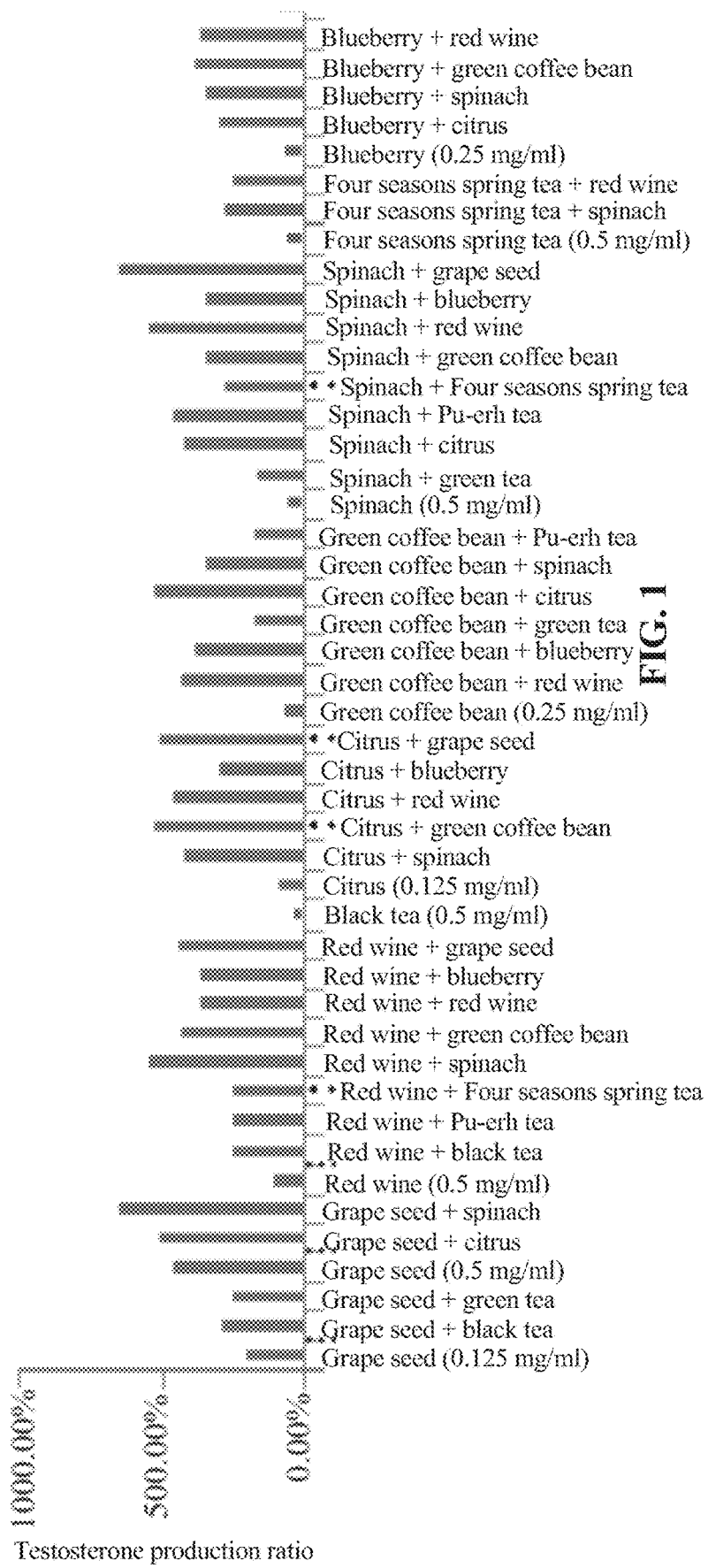
FIG. 1 is a diagram comparing the results of different plant extract combinations or combinations of components for testosterone secretion in an embodiment of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

EXAMPLE 1

Preparation of Plant Extracts 1-1 Preparation of Black Tea Extract

First, the black tea leaves (i.e. the fermented leaves of *Camellia sinensis*) were washed and dried, and the black tea leaves were coarsely crushed by a pulverizer. Next, the obtained crude black tea was extracted by using water as a solvent, and the solvent and the crude black tea were uniformly mixed at a liquid-solid ratio of 5-20:1-5. The extraction temperature is 50° C.-100° C. for 0.5-3 hours. In this example, the extraction temperature is preferably from 75° C.-95° C.

After the black tea extract obtained by the above extraction step was cooled to room temperature, it was filtered through a strainer of 400 mesh to remove residual solids. The filtered black tea extract can be further concentrated under reduced pressure at 45° C. to 70° C. to obtain a concentrated product.

1-2 Preparation of Green Tea Extract

First, the green tea leaves (i.e. the unfermented leaves of *Camellia sinensis*) were washed and dried, and the green tea leaves were coarsely crushed by a pulverizer. Next, the obtained crude green tea was extracted by using water as a solvent, and the solvent and the crude green tea were uniformly mixed at a liquid-solid ratio of 5-20:1-5. The extraction temperature is 50° C.-100° C. for 0.5-3 hours. In this example, the extraction temperature is preferably from 75° C.-95° C.

After the green tea extract obtained by the above extraction step was cooled to room temperature, it was filtered through a strainer of 400 mesh to remove residual solids. The filtered green tea extract can be further concentrated under reduced pressure at 45° C. to 70° C. to obtain a concentrated product.

1-3 Preparation of Four Seasons Spring Tea Extract

The leaves of the Four seasons spring tea plant were washed and dried, and the Four seasons spring tea leaves were coarsely crushed by a pulverizer. Next, the obtained crude Four seasons spring tea was extracted by using water as a solvent, and the solvent and the crude Four seasons spring tea were uniformly mixed at a liquid-solid ratio of 5-20:1-5. The extraction temperature is 50° C.-100° C. for 0.5-3 hours. In this example, the extraction temperature is preferably from 75° C.-95° C.

After the Four Seasons Spring tea extract obtained by the above extraction step was cooled to room temperature, it was filtered through a strainer of 400 mesh to remove residual solids. The filtered Four Seasons Spring tea extract can be further concentrated under reduced pressure at 45° C. to 70° C. to obtain a concentrated product.

1-4 Preparation of Other Plant Extracts

The remaining extracts were obtained from commercial products including: the grape seed extract (extracted from *Vitis* spp. plant seeds, purchased from Guarante Biotech Co., Ltd.), the citrus extract (extracted from the *Citrus reticulata* fruit, purchased from LAWTON Trading Co., Ltd.), the spinach extract (extracted from *Spinacia oleracea*, purchased from HONHSIANG FARM PRODUCTS FACTORY), the Pu-erh tea extract (extracted from post-fermented leaves of *Camellia Sinensis*, purchased from Nanjing Zelang Biotechnology Co., Ltd.), the green coffee bean extract (extracted from seeds of unroasted *Coffea* spp., purchased from ARJUNA NATURAL EXTRACTS Ltd. (India)), the red wine extract (extracted from red wine, purchased from Shanghai Boyoutang Biotechnology Co., Ltd.), the blueberry extract (extracted from the *Vaccinium Cyanococcus* fruit, purchased from Biomed Herbal Research Co., Ltd.), the broccoli sprout extract (extracted from *Brassica oleracea* var. *italica* seedlings, purchased from CHORI CO., LTD.), the ginseng extract (extracted from the root of *Panax ginseng*, purchased from Hunan Huacheng Biotech, Inc), the wolfberry extract (extracted from the *Lycium chinense* fruit, purchased from Hunan Hua Kang Biotechnology Co., Ltd.), the aloe extract (extracted from *Aloe vera*, purchased from Biomed Herbal Research Co., Ltd.), the rosemary extract (extracted from *Rosmarinus officinalis*, purchased from Jiajing Baica Co., Ltd.), the turmeric extract (extracted from *Curcuma longa*, purchased from ARJUNANATURALEXTRACTS LTD), the red clover extract (extracted from *Trifolium pretense*, purchased from Material World Industrial Co. Ltd.), the garlic extract (extracted from *Allium sativum* bulbs, purchased from Changsha Huir Biological-tech Co., Ltd.). These extracts are formulated in water at appropriate concentrations for use.

EXAMPLE 2

Preparation of Other Components of Composition

The other components of the composition were also obtained from commercial products, wherein the beta carotene was purchased from Juyan Trading Co., Ltd., and the lycopene was purchased from Hunan Naturalin Bio-Resources Co., Ltd.. The components are formulated in water at appropriate concentrations for use.

EXAMPLE 3

Test of Effects of Plant Extracts or Combinations of Components on Testosterone Secretion The mouse Leydig cells (hereinafter referred to as TM3 cells, ATCC CRL1714) were prepared and cultured in the cell culture medium (Ham's F12 medium and Dulbecco's modified Eagle's medium (Gibco) containing 5% horse serum, 2.5% fetal bovine serum, 0.5 mM sodium pyruvate, 15 mM HEPES and 1% Penicillin/streptomycin, mixed at a ratio of 1:1). 500 µl of the cell culture medium was added to each well of a 24-well plate to have $2 \times 10^4$ TM3 cells per well, and cultured at 37° C. for 24 hours. After the cells were adhered, the original medium was removed, and 500 µl of the aforementioned fresh cell culture medium was added.

The samples were then divided into two groups, of which group A was the control group, and no plant extracts or other test components were added. Group B was the test group. In group B, according to the plant extracts and component types listed in Tables 1 to Table 3, respectively, at doses of 0.03125 mg/ml to 4 mg/ml, single extract/components, or two extracts, the extracts/components prepared in Example 1 or Example 2 were added in a ratio of 1:1, and then reacted at 37° C. for 24 hours. After that, the condition of the amount of testosterone secretion was analyzed. The doses shown in the tables are the doses of the single extract, or the combination of the extracts.

First, 50 µl of the supernatant of the culture medium after the reaction of each of the above groups was taken out, and the testosterone ELISA test kit (USCN, Cat# CEA458Ge) was used to detect the testosterone concentration. The detected values were then analyzed by Microsoft Excel software using Student's t-test to determine whether there is statistical significance between the two samples (* indicates p-value <0.05;  indicates p-value <0.01; * indicates p-value <0.001). The results of the changes in the aforementioned testosterone concentrations are shown in Table 1, Table 2, FIG. 1 and FIG. 2, respectively.

TABLE 1

| Plant extract/ composition | dose/ratio | Increase in testosterone secretion | Plant extract/ composition | dose/ratio | Increase in testosterone secretion |
| --- | --- | --- | --- | --- | --- |
| grape seed | 0.125 mg/ml | 205.13% | citrus + blueberry | 0.125 mg/ml (1:1) | 301.82% |
| grape seed + black tea | 0.125 mg/ml (1:1) | 291.63% | citrus + grape seed | 0.5 mg/ml (1:1) | 513.44% |
| grape seed + green tea | 0.125 mg/ml (1:1) | 252.60% | green coffee bean | 0.25 mg/ml | 72.60% |
| grape seed | 0.5 mg/ml | 462.78% | green coffee bean + red wine | 0.25 mg/ml (1:1) | 431.90% |
| grape seed + citrus | 0.5 mg/ml (1:1) | 513.44% | green coffee bean + blueberry | 0.25 mg/ml (1:1) | 382.36% |
| grape seed + spinach | 0.5 mg/ml (1:1) | 654.40% | green coffee bean + green tea | 1 mg/ml (1:1) | 171.07% |
| red wine | 0.5 mg/ml | 117.34% | green coffee bean + citrus | 0.25 mg/ml (1:1) | 525.31% |
| red wine + black tea | 0.5 mg/ml (1:1) | 252.08% | green coffee bean + spinach | 1 mg/ml (1:1) | 345.70% |
| red wine + Pu-erh tea | 0.5 mg/ml (1:1) | 247.71% | green coffee bean + Pu-erh tea | 1 mg/ml (1:1) | 169.75% |
| red wine + Four seasons spring tea | 0.5 mg/ml (1:1) | 251.08% | spinach | 0.5 mg/ml | 67.28% |
| red wine + spinach | 0.5 mg/ml (1:1) | 550.65% | spinach + green tea | 0.5 mg/ml (1:1) | 162.33% |
| red wine + green coffee bean | 0.5 mg/ml (1:1) | 431.90% | spinach + citrus | 0.5 mg/ml (1:1) | 426.99% |
| red wine + red wine | 0.5 mg/ml (1:1) | 369.92% | spinach + Pu-erh tea | 0.5 mg/ml (1:1) | 463.94% |
| red wine + blueberry | 0.5 mg/ml (1:1) | 369.92% | spinach + Four seasons spring tea | 0.5 mg/ml (1:1) | 279.38% |
| red wine + grape seed | 0.5 mg/ml (1:1) | 446.62% | spinach + green coffee bean | 1 mg/ml (1:1) | 345.70% |
| citrus | 0.125 mg/ml | 97.92% | spinach + red wine | 0.25 mg/ml (1:1) | 550.65% |
| citrus + spinach | 0.5 mg/ml (1:1) | 426.99% | spinach + blueberry | 0.5 mg/ml (1:1) | 349.28% |
| citrus + green coffee bean | 0.25 mg/ml (1:1) | 525.31% | spinach + grape seed | 0.5 mg/ml (1:1) | 654.40% |
| citrus + red wine | 0.5 mg/ml (1:1) | 465.76% | | | |

TABLE 2

| Plant extract/component | dose | Increase in testosterone secretion | Plant extract/composition | dose/ratio | Increase in testosterone secretion |
|---|---|---|---|---|---|
| broccoli sprout | 0.25 mg/ml | 92.26% | broccoli sprout + lycopene | 0.25 mg/ml (1:1) | 258.51% |
| apple polyphenols | 0.03125 mg/ml | 91.89% | apple polyphenols + turmeric | 0.03125 mg/ml (1:1) | 258.91% |
|  | 0.25 mg/ml | 183.44% | apple polyphenols + broccoli sprout | 0.25 mg/ml (1:1) | 291.25% |
| beta carotene | 0.03125 mg/ml | 66.21% | beta carotene + turmeric | 0.03125 mg/ml (1:1) | 215.27% |
|  | 0.125 mg/ml | 103.79% | beta carotene + lycopene | 0.125 mg/ml (1:1) | 227.98% |
|  | 0.25 mg/ml | 111.42% | beta carotene + broccoli sprout | 0.25 mg/ml (1:1) | 240.61% |
| ginseng | 0.03125 mg/ml | 114.78% | ginseng + turmeric | 0.03125 mg/ml (1:1) | 297.97% |
|  | 0.25 mg/ml | 116.90% | ginseng + lycopene | 0.25 mg/ml (1:1) | 322.37% |
| wolfberry | 0.25 mg/ml | 121.85% | ginseng + broccoli sprout | 0.25 mg/ml (1:1) | 343.29% |
| aloe | 0.25 mg/ml | 108.80% | ginseng + beta carotene | 0.25 mg/ml (1:1) | 270.67% |
| rosemary | 0.03125 mg/ml | 106.84% | wolfberry + beta carotene | 0.25 mg/ml (1:1) | 257.52% |
|  | 0.25 mg/ml | 48.43% | wolfberry + ginseng | 0.25 mg/ml (1:1) | 269.71% |
| lycopene | 0.25 mg/ml | 104.02% | aloe + red clover | 0.25 mg/ml (1:1) | 278.95% |
|  | 0.125 mg/ml | 99.94% | rosemary + turmeric | 0.03125 mg/ml (1:1) | 263.63% |
| turmeric | 0.03125 mg/ml | 111.89% | rosemary + wolfberry | 0.25 mg/ml (1:1) | 186.73% |
| red clover | 0.25 mg/ml | 89.32% | rosemary + garlic | 0.25 mg/ml (1:1) | 186.70% |
| garlic | 0.25 mg/ml | 128.88% | rosemary + red clover | 0.25 mg/ml (1:1) | 156.70% |

TABLE 3

| Plant extract/component | dose | Increase in testosterone secretion | Plant extract/component | dose | Increase in testosterone secretion |
|---|---|---|---|---|---|
| grape seed | 0.5 mg/ml | 462.78% | blueberry | 4 mg/ml | 41.01% |
|  | 0.125 mg/ml | 205.13% |  | 2 mg/ml | 59.86% |
| red wine | 0.5 mg/ml | 117.34% |  | 1 mg/ml | 64.04% |
|  | 0.25 mg/ml | 75.59% |  | 0.5 mg/ml | 83.72% |
| citrus | 4 mg/ml | 87.57% |  | 0.25 mg/ml | 75.69% |
|  | 2 mg/ml | 100.22% |  | 0.125 mg/ml | 80.62% |
|  | 1 mg/ml | 81.43% | black tea | 2 mg/ml | 10.18% |
|  | 0.5 mg/ml | 78.36% |  | 1 mg/ml | 15.18% |
|  | 0.25 mg/ml | 76.82% |  | 0.5 mg/ml | 29.11% |
|  | 0.125 mg/ml | 97.92% |  | 0.25 mg/ml | 56.37% |
| green coffee bean | 1 mg/ml | 35.01% |  | 0.125 mg/ml | 71.93% |
|  | 0.5 mg/ml | 46.77% | green tea | 1 mg/ml | 15.39% |
|  | 0.25 mg/ml | 72.60% |  | 0.5 mg/ml | 21.33% |
| spinach | 2 mg/ml | 81.57% |  | 0.25 mg/ml | 45.02% |
|  | 1 mg/ml | 61.58% |  | 0.125 mg/ml | 45.15% |
|  | 0.5 mg/ml | 67.28% | Pu-erh tea | 4 mg/ml | 9.67% |
|  | 0.25 mg/ml | 98.45% |  | 2 mg/ml | 21.01% |
| Four seasons spring tea | 4 mg/ml | 15.51% |  | 1 mg/ml | 54.71% |
|  | 1 mg/ml | 70.74% |  | 0.5 mg/ml | 78.47% |
|  | 0.5 mg/ml | 57.57% |  | 0.25 mg/ml | 91.57% |
|  | 0.25 mg/ml | 61.40% | control | — | 100% |

Figure 2:
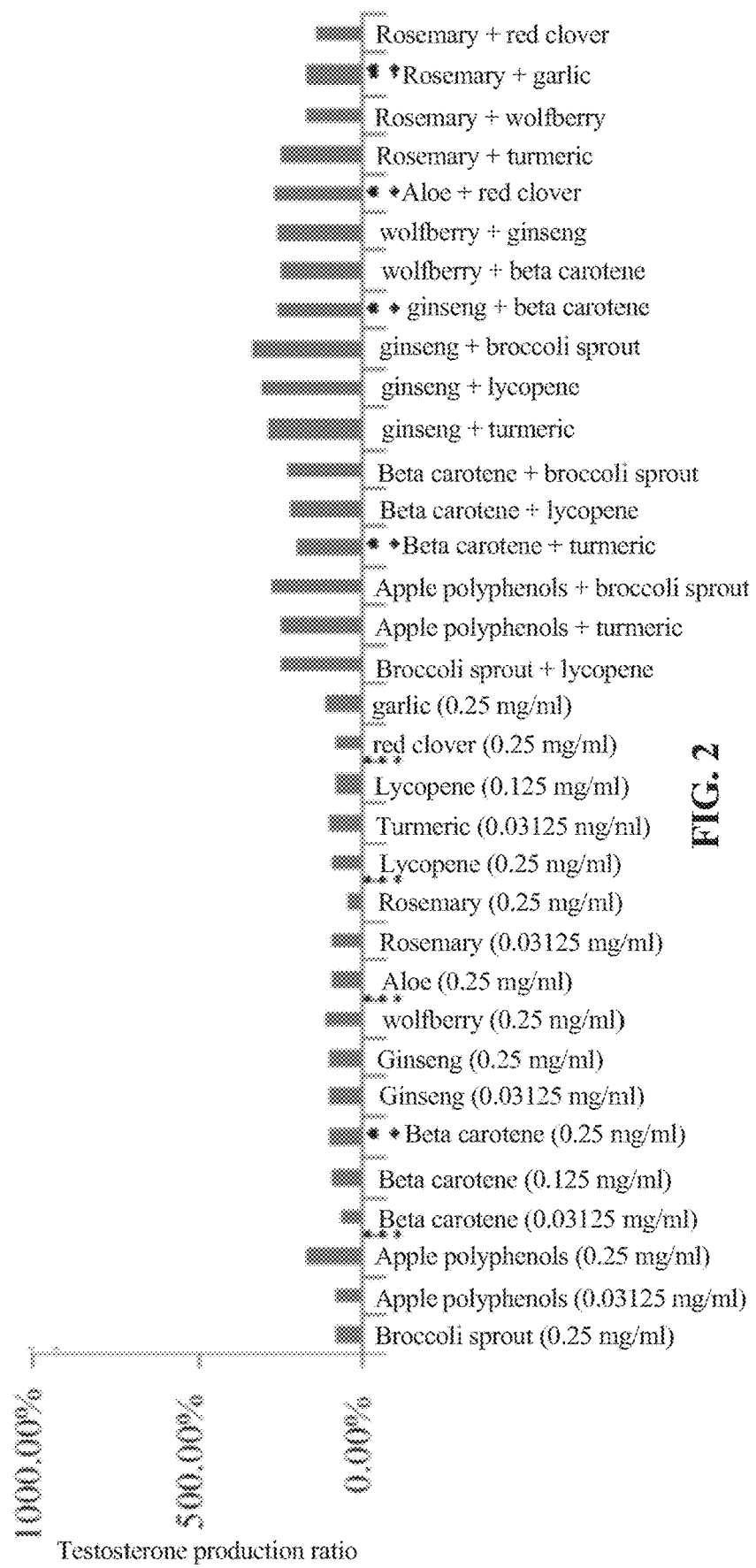
FIG. 2 is a diagram comparing the results of another plant extract combination or combination of components for testosterone secretion in an embodiment of the present invention.

Table 1 and Table 2 are lists of changes in testosterone concentration after combination of plant extracts or combinations of plant extracts and components, respectively. FIG. 1 and FIG. 2 are comparative histogram graphically shown in Table 1 and Table 2. As shown in Table 1 and FIG. 1, the promoting effect of the grape seed extract alone (0.125 mg/ml) is 205.13%, but in combination with the black tea extract (0.125 mg/ml, the promoting effect is 29.11%) or the green tea extract (0.125 mg/ml, the promoting effect is 45.15%), it could be increased to 291.63% and 252.60%, respectively. The 0.5 mg/ml of grape seed extract was combined with the citrus extract (0.5 mg/ml, the promoting effect is 97.92%) or the spinach extract (0.5 mg/ml, the promoting effect is 67.28%), the promoting effect could be increased to 513.44% and 654.40%. From the above results, the composition comprising a combination of the grape seed extract and the black tea extract, the grape seed extract and the green tea extract, the grape seed extract and the citrus extract, or the grape seed extract and the spinach extract can significantly improve the secretion of testosterone.

On the other hand, the red wine extract alone (0.5 mg/ml) promoted the secretion of testosterone only 117.34%, but in combination with 0.5 mg/ml black tea extract (the promoting effect is 29.11%), the Pu-erh tea extract (the promoting effect is 78.47%), the Four Seasons Spring tea extract (the promoting effect is 57.57%), the spinach extract (the promoting effect is 67.28%), the green coffee bean extract (the promoting effect is 46.77%), the blueberry extract (the promoting effect is 83.72%), or the grape seed extract (the promoting effect is 462.78%), the testosterone secretions were increased by 252.08%, 247.71%, 251.08%, 550.65%, 431.90%, 369.92%, 369.92%, and 446.62%, respectively. From the above results, the composition comprising a combination of the red wine extract and the black tea extract, the red wine extract and the Pu-erh tea extract, the red wine extract and the Four Seasons Spring tea extract, the red wine extract and the spinach extract, the red wine extract and the green coffee bean extract, the red wine extract and the blueberry extract, or the red wine extract and the grape seed extract has a more pronounced effect on the promotion of testosterone secretion.

In addition, the promoting effects of the citrus extract alone (0.125, 0.25, and 0.5 mg/ml) on the secretion of testosterone was only 97.92%, 76.82%, and 78.36%, but in combination with the spinach extract (0.5 mg/ml, the promoting effect is 67.28%), the green coffee bean extract (0.25 mg/ml, the promoting effect is 72.01%), the red wine extract (0.5 mg/ml, the promoting effect is 117.34%), the blueberry extract (0.125 mg/ml, the promoting effect is 80.62%), or the grape seed extract (0.5 mg/ml, the promoting effect is 462.78%), the testosterone secretions were increased by 426.99%, 525.31%, 465.76%, 301.82%, and 513.44%, respectively. From the above results, the composition comprising a combination of the citrus extract and the spinach extract, the citrus extract and the green coffee bean extract, the citrus extract and the red wine extract, the citrus extract and the blueberry extract, or the citrus extract and the grape seed extract has a remarkable effect on the promotion of testosterone secretion.

Similarly, the green coffee bean extract alone (0.25, 1 mg/ml) promoted the secretion of testosterone only by 72.60% and 35.01%, but in combination with the red wine extract (0.25 mg/ml, the promoting effect is 75.59%), the blueberry extract (0.25 mg/ml, the promoting effect is 75.69%), the green tea extract (1 mg/ml, the promoting effect is 15.39%), the citrus extract (0.25 mg/ml, the promoting effect is 76.82%), the spinach extract (1 mg/ml, the promoting effect is 61.58%), or the Pu-erh tea extract (1 mg/ml, the promoting effect is 54.71%), the testosterone secretions were increased by 431.90%, 382.36%, 171.07%, 525.31%, 345.70%, and 169.75%, respectively. From the above results, the composition comprising a combination of the green coffee bean extract and the blueberry extract, the green coffee bean extract and the green tea extract, the green coffee bean extract and the spinach extract, or the green coffee bean extract and the Pu-erh tea extract also has a remarkable effect on the promotion of testosterone secretion.

Further, the promoting effects of the spinach extract alone (0.25, 0.5, 1 mg/ml) on the secretion of testosterone were 98.45%, 67.28% and 61.58%, respectively, but in combination with the green tea extract (0.5 mg/ml, the promoting effect is 21.33%), the citrus extract (0.5 mg/ml, the promoting effect is 78.36%), the Pu-erh tea (0.5 mg/ml, the promoting effect is 78.4%), the Four Seasons Spring tea extract (0.5 mg/ml, the promoting effect is 57.57%), the green coffee bean extract (1 mg/ml, the promoting effect is 35.01%), the red wine extract (0.25 mg/ml, the promoting effect is 75.59%), the blueberry extract (0.5 mg/ml, the promoting effect is 83.72%), or the grape seed extract (0.5 mg/ml, the promoting effect is 462.78%), the testosterone secretions were increased by 162.33%, 426.99%, 463.94%, 279.38%, 345.70%, 550.65%, 349.28%, and 654.40%, respectively. From the above results, the composition comprising a combination of the spinach extract and the green tea extract, the spinach extract and the citrus extract, the spinach extract and the Pu-erh tea extract, the spinach extract and the Four Seasons Spring tea extract, the spinach extract and the blueberry extract, or the spinach extract and the grape seed extract also has a very good effect on the promotion of testosterone secretion.

As shown in Table 2 and FIG. 2, the promoting effect of the broccoli sprout extract (0.25 mg/ml) on the secretion of testosterone was only 92.26%, but in combination with lycopene (0.25 mg/ml, the promoting effect is 104.02%), it can increase the secretion of testosterone by 258.51%. Apple polyphenols (0.03125 mg/ml) alone promoted testosterone secretion only 91.89%, but in combination with the turmeric extract (0.03125 mg/ml, the promoting effect is 111.89%), or the broccoli sprout extract (0.25 mg/ml, the promoting effect is 92.26%), the testosterone secretions were increased by 258.91% and 291.25%, respectively. From the above results, it is known that the composition comprising the broccoli sprout extract and the lycopene, the apple polyphenols and the turmeric extract, or the apple polyphenols and the broccoli sprout extract has a good effect on the increase of testosterone secretion.

On the other hand, the promoting effects of beta carotene alone (0.03125, 0.125, 0.25 mg/ml) on the secretion of testosterone were only 66.21%, 103.79%, 111.42%, but in combination with the turmeric extract (0.03125 mg/ml, the promoting effect is 111.89%), lycopene (0.125 mg/ml, the promoting effect is 99.94%), or the broccoli sprout extract (0.25 mg/ml, the promoting effect is 104.02%), the testosterone secretions were increased by 215.27%, 227.98%, and 240.61%. From the above results, it is known that the composition comprising a combination of beta carotene and the turmeric extract, beta carotene and lycopene, or beta carotene and the broccoli sprout extract has a good effect on the improvement of testosterone secretion.

The promoting effects of the ginseng extract alone (0.03125, 0.25 mg/ml) on the secretion of testosterone were only 114.78%, 116.9%, but in combination with the turmeric extract (0.03125 mg/ml, the promoting effect is 111.89%), lycopene (0.25 mg/ml, the promoting effect is 104.02%), the broccoli sprout extract (the promoting effect is 92.26%), or beta carotene (0.25 mg/ml, the promoting effect is 111.42%), the testosterone secretions were increased by 297.97%, 322.37%, 343.29%, and 270.67%, respectively. Similarly, the promoting effect of the wolfberry extract alone (0.25 mg/ml) on the secretion of testosterone was only 121.85%, but in combination with beta carotene (0.25 mg/ml, the promoting effect is 111.42%), or the ginseng extract (0.25 mg/ml, the promoting effect is 116.9%), the testosterone secretions were increased by 257.52% and 269.71%, respectively. From the above results, the composition comprising a combination of the ginseng extract and the turmeric extract, the ginseng extract and lycopene, the ginseng extract and the broccoli sprout extract, the ginseng extract and beta carotene, the wolfberry extract and beta carotene, or the wolfberry extract and the ginseng extract has a good effect on the increase of testosterone secretion.

The promoting effect of the aloe extract alone (0.25 mg/ml) on the secretion of testosterone was only 108.8%, but in combination with the red clover extract (0.25 mg/ml, the promoting effect is 89.32%), the testosterone secretions were increased by 278.95%. Finally, the promoting effects of the rosemary extract alone (0.03125, 0.25 mg/ml) on the secretion of testosterone were only 106.84% and 48.43%, but in combination with the turmeric extract (0.03125 mg/ml, the promoting effect is 111.89%), the wolfberry extract (0.25 mg/ml, the promoting effect is 121.85%), the garlic extract (0.25 mg/ml, the promoting effect is 128.88%), or the red clover extract (0.25 mg/ml, the promoting effect is 89.32%), the secretion of testosterone was increased by 263.63%, 186.73%, 186.70%, and 156.70%, respectively. From the above results, the composition comprising a combination of the aloe extract and the red clover extract, the rosemary extract and the turmeric extract, the rosemary extract and the wolfberry extract, the rosemary extract and the garlic extract, or the rosemary extract and the red clover extract has a good effect on the increase of testosterone secretion.

It can be seen from the above tests that the composition having the function of promoting testosterone secretion in the embodiment of the present invention can produce an unexpected multiplication effect when the two extracts or the extract and the component are combined. The secretion of testosterone is significantly increased. Accordingly, the composition can be utilized to prepare related pharmaceutical or food compositions that provide an improvement in the quality of the sexual characteristics or muscle and bone density of the applicator or consumer.

Further, the composition providing the function of promoting testosterone secretion according to an embodiment of the present invention may be further added to a food, a health food, a dietary supplement or a drink. When the composition providing the function of promoting testosterone secretion according to an embodiment of the present invention is prepared as a pharmaceutical composition, the pharmaceutical composition may be further added to a carrier or other adjuvants well known in the art. The dosage form of the pharmaceutical composition can be, but is not limited to, a solution, a capsule, or a lozenge.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for promoting secretion of testosterone, comprising administering to a subject in need thereof an effective amount of a composition comprising 0.5 mg/ml of a red wine extract and 0.5 mg/ml of a Four Seasons Spring tea extract.

2. The method according to claim 1, wherein the composition is a pharmaceutical composition for promoting secretion of testosterone.

3. The method according to claim 1, wherein the composition is a food product, a health food, a dietary supplement or a drink for promoting secretion of testosterone.

* * * * *